United States Patent
Tschöpe et al.

(10) Patent No.: US 10,144,777 B2
(45) Date of Patent: Dec. 4, 2018

(54) B-LYMPHOCYTE TARGETING AGENTS FOR USE IN A METHOD FOR THE TREATMENT OF A DISEASE

(75) Inventors: Carsten Tschöpe, Berlin (DE); H. P. Schultheiss, Berlin (DE); Felicitas Escher, Berlin (DE); Hans-Dieter Volk, Berlin (DE); Petra Reinke, Berlin (DE)

(73) Assignee: Charité—Universitätsmedizin Berlin, Berlin (DE)

(*) Notice: Subject to any disclaimer, the term of this patent is extended or adjusted under 35 U.S.C. 154(b) by 0 days.

(21) Appl. No.: 13/264,090

(22) PCT Filed: Apr. 16, 2010

(86) PCT No.: PCT/EP2010/002362
§ 371 (c)(1),
(2), (4) Date: Dec. 22, 2011

(87) PCT Pub. No.: WO2010/118890
PCT Pub. Date: Oct. 21, 2010

(65) Prior Publication Data
US 2012/0100069 A1    Apr. 26, 2012

(30) Foreign Application Priority Data
Apr. 16, 2009 (EP) .................... 09005424

(51) Int. Cl.
| | |
|---|---|
| A61K 38/36 | (2006.01) |
| A61K 39/395 | (2006.01) |
| A61K 38/00 | (2006.01) |
| C07K 16/28 | (2006.01) |
| A61K 49/00 | (2006.01) |
| G01N 33/569 | (2006.01) |
| A61K 47/68 | (2017.01) |

(52) U.S. Cl.
CPC .... *C07K 16/2803* (2013.01); *A61K 39/39541* (2013.01); *A61K 47/6849* (2017.08); *A61K 49/0002* (2013.01); *A61K 49/0004* (2013.01); *C07K 16/2896* (2013.01); *G01N 33/56972* (2013.01); *G01N 2800/325* (2013.01); *G01N 2800/52* (2013.01)

(58) Field of Classification Search
CPC .................. C07K 16/2887; A61K 39/39541
See application file for complete search history.

(56) References Cited

U.S. PATENT DOCUMENTS

2006/0263349 A1* 11/2006 McCutcheon et al. .................... G01N 33/564
424/131.1

FOREIGN PATENT DOCUMENTS

| JP | 2001-503253 A | 3/2001 |
| JP | 2008-540678 A | 11/2008 |
| WO | WO 2005/113003 | 12/2005 |
| WO | WO 2006/133450 | 12/2006 |
| WO | WO 2008/031056 | 3/2008 |

OTHER PUBLICATIONS

Keren et al., "Late Humoral Rejection in a Cardiac Transplant Recipient Treated With the Anti-CD20 Monoclonal Antibody Rituximab", Transplantation Proceedings, 38, 1520-1522 (2006).*
Koukoulaki et al., "Remission of refractory hepatitis C-negative cryoglobulinaemic vasculitis after rituximab and infliximab" Nephrol Dial Transplant (2005) 20: 213-216 doi:10.1093/ndt/gfh564.*
Karras et al., "Cryoglobulin-Induced Cardiomyopathy", Journal of the American College of Cardiology, vol. 55, No. 7, 2010 ISSN 0735-1097/10/$36.00 doi:10.1016/j.jacc.2009.09.042, Downloaded From: http://content.onlinejacc.org/ on Dec. 2, 2015.*
Arbustini et al., "Ten-year experience with endomyocardial biopsy in myocarditis presenting with congestive heart failure: frequency, pathologic characteristics, treatment and follow-up", *Giornale Italiano di Cardologia*, 1997, vol. 27, pp. 209-223.
Bartlett et al., "Type I IFN-β gene therapy suppresses cardiac $CD8^+$T-cell infiltration during autoimmune myocarditis", *Immunology and Cell Biology*, 2004, vol. 82, pp. 119-126.
Lenzo et al., "Characteristics of Murine Cytomegalovirus Myocarditis: Cellular Infiltration of the Heart and Virus Persistence", *Journal of Molecular and Cellular Cardiology*, 2002, vol. 34, pp. 629-640.
Nikolaidis et al., "When Cancer and Heart Failure Cross Paths: A Case report of Severe Cardiorenal Compromise Associated with the Anti-CD20 Monoclonal Antibody Rituximab in a Patient with Dilated Cardiomyopathy", *Congestive Heart Failure*, 2001, vol. 7, pp. 223-227.
Touma et al., "Successful treatment of cardiac involvement in dermatomyositis with rituximab", *Joint Bone Spine*, 2008, vol. 75, pp. 334-337.
Afanasyeva et al., "Quantitative Analysis of Myocardial Inflammation by Flow Cytometry in Murine Autoimmune Myocarditis: Correlation with Cardiac Function", *The American Journal of Pathology*, Mar. 2004, vol. 164, No. 3, pp. 807-815.
Fernandes, "The Myocardium of Fetuses with Endocardial Fibroelastosis Contains a Paucity of B and T Cells Compared with Normal Controls", *Journal of the American College of Cardiology*, Mar. 2009, vol. 55, No. 10A, pp. A44.E422.
Holzinger, Christoph et al., "Phenotypic Patterns of Mononuclear Cells in Dilated Cardiomyopathy," *Circulation*, 1995, vol. 92, p. 2876-2885.
Baran, D.A. et al., "Refractory Humoral Cardiac Allograft Rejection Successfully Treated With a Single Dose of Rituximab," *Transplantation Proceedings*, 2004, 36:3164-3166.
Brihaye, Benoit et al., "Rituximab reversed cardiac involvement of Wegener's granulomatosis: magnetic resonance imaging assessment," *Presse Med.*, 2008, 37:412-415.

(Continued)

*Primary Examiner* — Michail A Belyavskyi
(74) *Attorney, Agent, or Firm* — Saliwanchik, Lloyd & Eisenschenk

(57) ABSTRACT

The present invention is related to a B-lymphocyte targeting agent for use in a method for the treatment or diagnosis of cardiac insufficiency. Furthermore, it is related to a composition comprising such B-lymphocyte targeting agent and methods for determining whether a patient suffering from cardiac insufficiency is amenable to the use of the B-lymphocyte targeting agent for its treatment.

21 Claims, 5 Drawing Sheets

(56) References Cited

OTHER PUBLICATIONS

English translation of Office Action issued in corresponding Japanese Application No. 2012-505094, dated Jun. 2, 2015.
Kaizawa, Yukitoshi etal., "Successful Chemotherapy Treatment of PriMary Cardiac Lymphoma Diagnosed by CT-Guided Transthoracic Percutaneous Needle Biopsy," *Annals of Kurashiki Central Hospital (Kurashiki Chuobyoin Nenpou)*, 2007, vol. 70, pp. 173-179.
Koga, Yoshinori et al., "Lymphocyte Subsets in Patients with Acute Myopericarditis Arrhythmias and Dilated Cardiomyopathy," Japanese Circulation Journal, Jan. 1989, vol. 53, pp. 78-86.
Office Action issued in corresponding Japanese Application No. 2012-505094, dated Jun. 2, 2015.

\* cited by examiner

B-LYMPHOCYTE TARGETING AGENTS FOR USE IN A METHOD FOR THE TREATMENT OF A DISEASE

CROSS REFERENCE TO A RELATED APPLICATION

This application is a National Stage Application of International Application Number PCT/EP2010/002362, filed Apr. 16, 2010; which claims priority to European Application No. 09005424.8, filed Apr. 16, 2009; which are incorporated herein by reference in their entirety.

The present invention is related to a B-lymphocyte targeting agent for use in a method for the treatment or diagnosis of cardiac insufficiency. Furthermore, it is related to a composition comprising such B-lymphocyte targeting agent and methods for determining whether a patient suffering from cardiac insufficiency is amenable to the use of the B-lymphocyte targeting agent for its treatment.

Cardiac insufficiency or heart failure is a disease which is characterized by a physiological state in which cardiac output is insufficient for the body's needs.

Common causes of heart failure include myocardial infarction and other forms of ischemic heart disease, hypertension, valvular heart disease and cardiomyopathy. Cardiomyopathies are heart muscle diseases, which have been defined by their central hemodynamics and macropathology and have been divided in five major forms: dilated (DCM), hypertrophic (HCM), restrictive (RCM), right ventricular (RVCM) and non-classifiable cardiomyopathies (NCCM). Inflammatory cardiomyopathy (DCMi) is a specific cardiomyopathy entity of DCM, being defined by the proof of intramyocardial inflammation and/or viral infection in endomyocardial biopsies (EMBs).

Heart failure can cause a large variety of symptoms such as shortness of breath (typically worse when lying flat, which is called orthopnea), coughing, ankle swelling and reduced exercise capacity. Heart failure is often undiagnosed due to a lack of a universally agreed definition and challenges in definitive diagnosis. Treatment commonly consists of lifestyle measures (such as decreased salt intake) and medications, and sometimes devices or even surgery.

Heart failure is a common, costly, disabling and deadly condition. In developed countries, around 2% of adults suffer from heart failure, but among those over the age of 65, this rate increases to 6-10%. Mostly due to costs of hospitalization, it is associated with a high health expenditure; costs have been estimated to amount to 2% of the total budget of the National Health Service in the United Kingdom, and more than $35 billion in the United States. Heart failure is associated with significantly reduced physical and mental health, resulting in a markedly decreased quality of life. With the exception of heart failure caused by reversible conditions, the condition usually worsens with time. Although some patients survive many years, progressive disease is associated with an overall annual mortality rate of 10%.

Apart from lifestyle modalities, there are also current pharmacological modalities for the treatment of cardiac insufficiency.

There is a significant evidence-practice gap in the treatment of cardiac insufficiency; particularly the underuse of ACE inhibitors and β-blockers and aldosterone antagonists which have been shown to provide mortality benefit. Treatment of cardiac insufficiency aims to relieve symptoms, to maintain a euvolemic state (normal fluid level in the circulatory system), and to improve prognosis by delaying progression of heart failure and reducing cardiovascular risk. Drugs used include: diuretic agents, vasodilator agents, positive inotropes, ACE inhibitors, beta blockers, and aldosterone antagonists (e.g. spironolactone). Some drugs which increase heart function, such as the positive inotrope Milrinone, lead to increased mortality, and are contraindicated.

Therefore, the problem underlying the instant application is, in a first aspect, to provide an agent which is suitable for the treatment of cardiac insufficiency.

In a second aspect, the problem underlying the present invention is to provide an agent which is suitable to determine which kind of patient is amenable to a therapy based on the agent to be provided in accordance with the first aspect.

The problems underlying the present invention are solved by a B-lymphocyte targeting agent for use in a method for the treatment of cardiac insufficiency.

In one embodiment, the B-lymphocyte targeting agent is targeting an antigen expressed by a B-lymphocyte or an antigen which is inducible to be expressed by a B-lymphocyte.

In one embodiment the B-lymphocyte targeting agent is binding to an antigen expressed by a B-lymphocyte or an antigen which is inducible to be expressed by a B-lymphocyte.

In one embodiment, the antigen is selected from the group comprising CD19, CD20 and CD21.

In one embodiment, the antigen is CD20.

In one embodiment, the method comprises the step of administering the B-lymphocyte targeting agent to a patient in need thereof.

In one embodiment, the patient is one the heart tissue of which contains B-lymphocytes.

In one embodiment, the B-lymphocytes are present in the intercellular space, preferably the intercellular space between the heart muscle cells and the cells of the heart vasculature.

In one embodiment, the cardiac insufficiency is one selected from cardiac insufficiency caused by inflammation of the myocardium or endocardium, cardiac insufficiency caused by degeneration of the myocardium or the endocardium, cardiac insufficiency caused by coronary insufficiency, cardiac insufficiency caused by myocardial infarction and cardiac insufficiency caused by injury.

In one embodiment, the cardiac insufficiency is different from cardiac insufficiency caused by myocardial infarction.

In one embodiment, the cardiac insufficiency is caused by inflammation of the myocardium or endocardium In one embodiment of the present invention, said cardiac insufficiency is caused by a cardiomyopathy, preferably inflammatory cardiomyopathy (DCMi).

In one embodiment, the B-lymphocyte targeting agent is capable or useful in killing B-lymphocytes.

In one embodiment, the B-lymphocytes bear at least one antigen selected from the group comprising CD19, CD20 and CD21, preferably the antigen is CD20.

In one embodiment, the B-lymphocyte targeting agent is a naked B-lymphocyte targeting agent.

In one embodiment, the B-lymphocyte targeting agent comprises a further moiety which is useful in the killing of the B-lymphocyte.

In one embodiment, the further moiety is selected from the group comprising radioisotopes, cytotoxic agents and immunomodulators.

In one embodiment, the B-lymphocyte targeting agent is therapeutically effective or is administered in an amount such as to provide for a therapeutic effect.

In one embodiment, the B-lymphocyte targeting agent is selected from the group comprising antibody, aptamer, spiegelmer, antigen binding polypeptide and anticaline.

In one embodiment, the B-lymphocyte targeting agent is an antibody.

In one embodiment, the antibody is a polyclonal antibody.

In one embodiment, the antibody is a monoclonal antibody.

In one embodiment, the antibody is an antibody fragment, preferably an antibody fragment which binds to the same antigen and/or epitope as the respective antibody.

In one embodiment, the antibody fragment is one selected from the group comprising F(ab')2, F(ab)2, Fab', Fab, Fv, scFv and sFv.

In one embodiment, the antibody is a subhuman primate antibody, murine monoclonal antibody, chimeric antibody, humanized antibody or human antibody.

In one embodiment, the antibody mediates complement-mediated cytotoxicity and/or antibody-dependent cell-mediated cytotoxicity.

In one embodiment, the antibody is an anti-CD20 antibody.

In one embodiment, the antibody is rituximab.

In one embodiment, the B-lymphocyte targeting agent is selected from the group comprising aptamer, spiegelmer, antigen binding polypeptide and anticaline.

In one embodiment, the B-lymphocyte targeting agent comprises a further moiety which is useful in the killing of the B-lymphocyte.

In one embodiment, the further moiety is selected from the group comprising radioisotopes, cytotoxic agents and immunomodulators.

In one embodiment, the further moiety is a radioisotope.

In one embodiment, the radioisotope is selected from the group comprising $^{198}$Au, $^{32}$P, $^{125}$I, $^{131}$I, $^{90}$Y, $^{186}$Re, $^{188}$Re, $^{67}$Cu, $^{211}$At, $^{213}$Bi or $^{225}$Ac.

The problems underlying the present invention are also solved by a pharmaceutical composition comprising a B-lymphocyte targeting agent as defined above and a pharmaceutically acceptable carrier.

In one embodiment, the pharmaceutical composition is for use in a method for the treatment of cardiac insufficiency, preferably cardiac insufficiency as defined above.

The problems underlying the present invention are also solved by the use of a B-lymphocyte targeting agent as defined above for the manufacture of a medicament for the treatment of cardiac insufficiency, preferably cardiac insufficiency as defined above.

The problems underlying the present invention are also solved by an in vitro method for determining whether a patient suffering from cardiac insufficiency is susceptible to a treatment of cardiac insufficiency using a B-lymphocyte targeting agent as defined above, comprising the following steps:
  a) providing a heart tissue sample of the patient;
  b) contacting the sample with a B-lymphocyte targeting agent as defined above; and
  c) determining whether B-lymphocytes are contained in the sample.

In one embodiment, the patient can be treated using a B-lymphocyte targeting agent as defined above, if there are B-lymphocytes contained in the sample.

The problems underlying the present invention are also solved by a method for determining whether a patient suffering from cardiac insufficiency is susceptible to a treatment of cardiac insufficiency using a B-lymphocyte targeting agent as defined above, comprising the following steps:
  a) administering to the patient a B-lymphocyte targeting agent as defined above; and
  b) visualizing the B-lymphocytes targeted by the B-lymphocyte targeting agent as defined above.

In one embodiment, it is determined whether the B-lymphocytes are present in the heart, more preferably whether B-lymphocytes are present in the intercellular space, preferably the intercellular space between the heart muscle cells and the cells of the heart vasculature.

In one embodiment, the patient may be treated using the B-lymphocyte targeting agent as defined above in case the B-lymphocytes are present in the heart, more preferably present in the intercellular space, preferably the intercellular space between the heart muscle cells and the cells of the heart vasculature.

In one embodiment, the B-lymphocyte targeting agent as defined above bears a label which preferably allows the detection of the B-lymphocyte targeting agent in a sample, a tissue, an organ or an organism.

In one embodiment, the B-cells are visualized by in vivo imaging.

In one embodiment, the in vivo imaging is a method selected from the group comprising magnetic resonance imaging, positron emission tomography, single photon emission computed tomography and optical imaging.

The problems underlying the present invention are also solved by the B-lymphocyte targeting agent as defined above for use in a(n) (in vitro) method as defined above.

The problems underlying the present invention are also solved by the B-lymphocyte targeting agent as defined above for use in a method for the diagnosis of cardiac insufficiency as defined above.

The problems underlying the present invention are also solved by the use of the B-lymphocyte targeting agent as defined above, for the manufacture of a diagnostic agent, preferably for the diagnosis of cardiac insufficiency.

In one embodiment, the cardiac insufficiency is one which is amenable to a treatment using a B-lymphocyte targeting agent as defined above.

In another aspect, the present invention relates to a method of treatment of cardiac insufficiency as defined above, said method comprising the step of administering the B-lymphocyte targeting agent as defined above to a patient in need thereof.

The present inventors have surprisingly found that B-lymphocytes are present in the heart of patients who suffer form cardiac insufficiency. More specifically, the present inventors have found that B-lymphocytes are present in the intercellular space, preferably the intercellular space between the heart muscle cells and the cells of the heart vasculature. This kind of B-lymphocytes can be addressed both for therapeutic and diagnostic purposes by the use of one or several B-lymphocyte targeting agents. Experimental evidence for the feasibility of this diagnostic and in particular therapeutic approach may also be taken from successful treatment of renal disease using an B-lymphocyte targeting agent such as an anti-CD20 antibody. Like in the case of cardiac disease such renal disease is characterized by the presence of B-lymphocytes.

As preferably used herein, the B-lymphocyte targeting agent targets an antigen of a B-lymphocyte. Targeting an antigen as used herein preferably means establishing an interaction between the antigen and the B-lymphocyte targeting agent according to the present invention. Preferably such interaction is stable under physiological conditions such as the conditions existing in the sample, tissue, organ or organism where such interaction occurs. A particularly preferred embodiment of interaction is the binding of the antigen to the B-lymphocyte targeting agent.

As preferably used herein, a B-lymphocyte is any B-lymphocyte or any pre-cursor cell, such as a plasma cell. In a preferred embodiment, the B-lymphocyte expresses an antigen, or can be induced to express such antigen. A B-lymphocyte is also referred to as B cell.

Such antigen, regardless whether it is expressed by the B-lymphocyte or whether the B-lymphocyte can be induced to express such antigen, is preferably selected from the group comprising CD19, CD20 and CD21. More preferably such antigen is CD20 in any aspect of the present invention.

The CD20 molecule (also called human B-lymphocyte-restricted differentiation antigen or Bp35) is a hydrophobic transmembrane protein with a molecular weight of approximately 35 kD located on pre-B- and mature B-lymphocytes (Valentine, M. A., et al. J. Biol. Chem. 264(19) (1989) 11282-11287; and Einfield, D. A., et al. EMBO J. 7(3) (1988) 711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson, K. C., et al., Blood 63(6) (1984) 1424-1433) but is not found on hematopoietic stem cells, pro-B cells, normal plasma cells, or other normal tissues (Tedder, T. F., et al., J, Immunol. 135 (2) (1985) 973-979).

The 85 amino acid carboxyl-terminal region of the CD20 protein is located within the cytoplasm. The length of this region contrasts with that of other B cell-specific surface structures such as IgM, IgD, and IgG heavy chains or histocompatibility antigens class II α or β chains, which have relatively short intracytoplasmic regions of 3, 3, 28, 15, and 16 amino acids, respectively (Komaromy, M., et al., NAR 11 (1983) 6775-6785). Of the last 61 carboxy-terminal amino acids, 21 are acidic residues, whereas only 2 are basic, indicating that this region has a strong net negative charge. The GenBank Accession No. of human CD20 is NP_690605. It is thought that CD20 might be involved in regulating an early step(s) in the activation and differentiation process of B cells (Tedder et al., Eur. J. Immunol. 25 Vol. 16 (1986) 881-887) and could function as a calcium ion channel (Tedder, T. F., et al., J. Cell. Biochem. 14D (1990) 195).

CD19 is expressed on follicular dendritic cells and B cells. In fact, it is present on B cells from earliest recognizable B-lineage cells during development to B-cell blasts but is lost on maturation to plasma cells. It primarily acts as a B cell co-receptor in conjunction with CD21 and CD81. Upon activation, the cytoplasmic tail of CD19 becomes phosphorylated which leads to binding by Src-family kinases and recruitment of PI-3 kinase. CD19 is also referred to as B4. The sequence of human CD19 may be taken from the uniprot databank as P15391 or from NM_001770 for its mRNA sequence, and NP_001761 for its amino acid sequence.

CD21 which is also referred to as CR2 or C3DR, is a protein involved in the complement system. It binds to iC3b (inactive derivative of C3b), C3dg, or C3d. B cells have CD21 receptors on their surfaces, allowing the complement system to play a role in B-cell activation and maturation. CD21 on mature B cells form a complex with two other membrane proteins, CD19 and CD81 (=TAPA-1). The CD21-CD19-CD81 complex is often called the B cell co-receptor complex, because CD21 binds to antigens through attached C3d (or iC3b or C3dg) when the membrane IgM binds to the antigen. This results in the B cell to have greatly enhanced response to the antigen. The sequence of human CD21 may be taken from the uniprot databank as P20023 or from NM_001006658 for its mRNA sequence, and NP_001006659 for its amino acid sequence.

It will be acknowledged by a person skilled in the art that any form of cardiac insufficiency may, in principle, be treated. In a preferred embodiment, however, those forms of cardiac insufficiency may be treated which involve B-lymphocytes. Involvement as preferably understood and used herein means that such B-lymphocytes are associated with the cardiac insufficiency, either in a causal manner or a non-causal manner but still leading to the occurrence or aggravation of the symptoms associated with cardiac insufficiency.

It will also be understood that, in principle, such cardiac insufficiency may be treated according to the present invention irrespective of the etiology of the disease, preferably as long as the prerequisite of the presence of B-lymphocytes is given.

It will be acknowledged that a variety of classes of B-cell targeting agents can be generated which are suitable to address the antigen expressed, either directly or upon induction, by the B-lymphocytes. Such classes of B-lymphocyte targeting agents comprise antibodies, aptamers, spiegelmers, antigen binding polypeptides and anticalines.

Methods for the production of antibodies which are specific for an antigen of B-lymphocytes and more specifically CD20, CD19 and CD21, are known to the person skilled in the art. The same applies to monoclonal antibodies. See generally Kohler and Milstein, Nature 256: 495 (1975); Coligan et al. (eds.), CURRENT PROTOCOLS IN IMMUNOLOGY (John Wiley & Sons 1991). Briefly, monoclonal antibodies can be obtained by injecting mice with a composition comprising, for example, NCA-90, verifying the presence of antibody production by removing a serum sample, removing the spleen to obtain B-lymphocytes, fusing the B-lymphocytes with myeloma cells to produce hybridomas, cloning the hybridomas, selecting positive clones which produce the desired antibodies, culturing the clones that produce antibodies to the antigen and isolating the antibodies from the hybridoma cultures.

Monoclonal antibodies can be isolated and purified from hybridoma cultures by a variety of well-known techniques. Such isolation techniques include affinity chromatography with Protein-A Sepharose, size-exclusion chromatography, and ion-exchange chromatography. See Coligan et al. (eds.), CURRENT PROTOCOLS IN IMMUNOLOGY (John Wiley & Sons 1991); Baines et al., pages 79-104, METHODS IN MOLECULAR BIOLOGY (The Humana Press, Inc. 1992).

Methods for the generation of subhuman primate antibodies, chimeric antibodies, humanized antibodies or human antibodies are equally known in the art. In connection therewith a "chimeric antibody" is preferably a recombinant protein that contains the variable domains and complementary determining regions derived from a rodent antibody, while the remainder of the antibody molecule is derived from a human antibody, and "humanized antibodies" are preferably recombinant proteins in which murine complementarity determining regions of a monoclonal antibody have been transferred from heavy and light variable chains of a murine immunoglobulin into a human variable domain.

An "antibody fragment", as preferably used herein, is a portion of an antibody such as F (ab') 2, F(ab)2, F (ab), Fab', Fab, Fv, scFv and sFv and the like. Regardless of its structure, an antibody fragment binds with the same antigen that is recognized by the intact antibody. For example, an anti-CD20 monoclonal antibody fragment binds with an epitope of CD20.

The term "antibody fragment", as preferably used herein, also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

A "naked antibody" is either an entire antibody or an antibody fragment, which is not conjugated to a therapeutic agent or diagnostic agent. Naked antibodies include both polyclonal and monoclonal antibodies, as well as certain recombinant antibodies, such as chimeric and humanized antibodies.

Aptamers are D-nucleic acids which are either single stranded or double stranded and which specifically interact with a target molecule such as the antigens of the B-lymphocytes as described herein. The manufacture or selection of aptamers is, e.g., described in European patent EP 0 533 838 B1. Basically the following steps are realized. First, a mixture of nucleic acids, i.e. potential aptamers, is provided whereby each nucleic acid typically comprises a segment of several, preferably at least eight subsequent randomised nucleotides. This mixture is subsequently contacted with the target molecule whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e.g. polymerase chain reaction. These steps may be repeated several times resulting in a mixture having an increased ratio of nucleic acids specifically binding to the target from which the final binding nucleic acid is then optionally selected. These specifically binding nucleic acid(s) are referred to aptamers. It is obvious that at any stage of the method for the generation or identification of the aptamers samples of the mixture of individual nucleic acids may be taken to determine the sequence thereof using standard techniques. It is within the present invention that the aptamers may be stabilized, e.g. by introducing defined chemical groups which are known to one skilled in the art of generating aptamers. Such modification may for example reside in the introduction of an amino group at the 2'-position of the sugar moiety of the nucleotides. Aptamers are currently used as therapeutical agents. However, it is also within the present invention that the thus selected or generated aptamers may be used for diagnostic purposes.

The generation or manufacture of spiegelmers which may be used or generated according to the present invention using the antigens of the B-lymphocytes as described herein, is based on a similar principle. The manufacture of spiegelmers is described in the international patent application WO 98/08856 A2. Spiegelmers are L-nucleic acids, which means that they are composed of L-nucleotides rather than aptamers which are composed of D-nucleotides as aptamers are. Spiegelmers are characterized by the fact that they have a very high stability in biological systems and, comparable to aptamers, specifically interact with the target molecule against which they are directed. For the purpose of generating spiegelmers, a heterogonous population of D-nucleic acids is created and this population is contacted with the optical antipode of the target molecule, in the present case for example with the D-enantiomer of the naturally occurring L-enantiomer of the antigens of the B-lymphocytes as described herein. Subsequently, those D-nucleic acids are separated which do not interact with the optical antipode of the target molecule. However, those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

It is to be acknowledged that both aptamers and spiegelmers preferably bind to their target molecule by the three-dimensional structure adopted by them rather than through Watson-Crick base pairing between the aptamer and spiegelmer, respectively, and the target molecule.

A further class of medicaments as well as diagnostic agents which may be generated using the antigens of the B-lymphocytes as described herein, are peptides which bind thereto. Such peptides may be generated by using methods according to the state of the art such as phage display. Basically, a library of peptides is generated, such as in form of phages, and this kind of libraries is contacted with the target molecule, in the present case, for example, the antigens of the B-lymphocytes as described herein. Those peptides binding to the target molecule are subsequently removed, preferably as a complex with the target molecule, from the respective reaction. It is known to the one skilled in the art that the binding characteristics, at least to a certain extend, depend on the particularly realized experimental set-up such as the salt concentration and the like. After separating those peptides binding to the target molecule with a higher affinity or a bigger force, from the non-binding members of the library, and optionally also after removal of the target molecule from the complex of target molecule and peptide, the respective peptide(s) may subsequently be characterised. Optionally, prior to the characterisation an amplification step is realized, e.g. by propagating the peptide coding phages. The characterisation preferably comprises the sequencing of the target binding peptides. Basically, the peptides are not limited in their lengths, however, preferably peptides having a lengths from about 8 to 20 amino acids are preferably obtained in the respective methods. The size of the libraries may be about $10^2$ to $10^{18}$, preferably $10^8$ to $10^{15}$ different peptides, however, is not limited thereto.

A particular form of target binding polypeptides are the so-called "anticalines" which are, among others, described in the German patent application DE 197 42 706 A1.

It will be understood by a person skilled in the art that if used as a therapeutic agent, the B-lymphocyte targeting agent according to the present invention is therapeutically effective or administered in an amount such as to achieve a pharmaceutically relevant effect. It will be further understood by a person skilled in the art that the B-lymphocyte targeting agent is intended to kill the targeted B-lymphocytes, preferably those which are present in the heart tissue as described in more detail herein.

As preferably used herein, the term "killing of the B-lymphocytes" can in the various embodiments of the present invention have one or several of the following meanings: to arrest the growth of the B-lymphocytes, to induce self-destruction of the B-lymphocytes through a biological process such as apoptosis or others, or to mediate either directly or indirectly the lysis of the B-lymphocytes.

It will be understood that by the use of any of the B-lymphocyte targeting agents as described herein the B-lymphocytes can be addressed and the B-lymphocyte targeting agent be used to transport any payload to said B-lymphocyte whereby such payload causes or mediates such killing of the B-lymphocytes. Such payload can be a radioactive label, a cytotoxic agent or any suitable immunomodulator, as known to the ones skilled in the art. Methods to attach such payload to the B-lymphocyte targeting agent either directly or indirectly are known to the ones skilled in the art.

In case of the B-lymphocyte targeting agent being an antibody and more specifically a monoclonal antibody, the cell killing can be mediated through complement-mediated cytotoxicity and/or antibody-dependent cell-mediated cytotoxicity. It is within the skill of a person of the art to screen this type of antibodies binding specifically to any of the B-lymphocyte antigens described herein.

A preferred B-lymphocyte targeting agent is an anti-CD20 antibody showing complement-mediated cytotoxicity and/or antibody-dependent cell-mediated cytotoxicity. In the prior art various species of this kind of B-lymphocyte targeting agent are described with a particularly preferred one being rituximab which is commercially available under the trade name RITUXAN or MABTHERA.

The "rituximab" antibody is a genetically engineered chimeric human gamma 1 murine constant domain containing monoclonal antibody directed against the human CD20 antigen. This chimeric antibody contains human gamma 1 constant domains and is identified by the name "C2B8" in U.S. Pat. No. 5,736,137 (Andersen, et. al.), issued on Apr. 17, 1998, assigned to IDEC Pharmaceuticals Corporation. Rituximab is approved for the treatment of patients with relapsed or refracting low-grade or follicular, CD20-positive, B cell non-Hodgkin's lymphoma. In vitro mechanism of action studies have shown that rituximab exhibits human complement-dependent cytotoxicity (CDC) (Reiff, M. E., et. al, Blood 83(2) 435-445 (1994)). Additionally, it exhibits significant activity in assays that measure antibody-dependent cellular cytotoxicity (ADCC).

As to the administration regimen of the B-lymphocyte targeting agents according to the present invention, it will be acknowledged by a person skilled in the art that they will be within the ranges ordinarily used in the art for administration of this kind of agents and the optimum dosage can be determined by routine experiments.

It will be acknowledged that the B-lymphocyte targeting agents as described herein are also suitable for the diagnosis of cardiac dysfunction in its various forms and more particularly those forms where B-lymphocytes are involved as outlined herein. Similar to their therapeutic application, the B-lymphocyte targeting agents have to be labelled either directly or indirectly so as to allow the detection of the B-lymphocytes targeted by the B-lymphocyte targeting agents.

As also disclosed herein, the B-lymphocyte targeting agents described herein are suitable to stratify a group of patients suffering from or being at risk of suffering from cardiac heart failure, and to determine whether and if so which member of said group may be treated in accordance with the present invention, by the administration of the B-lymphocyte targeting agent.

In vivo imaging methods are known to the ones skilled in the art and, for example, described in European patent application EP 01114110.8.

The term "ejection fraction (EF)", as used herein, is the fraction of blood pumped out of the ventricles with each heart beat. Healthy individuals typically have ejection fractions between 50% and 65%, wherein normal values also depend on the modality being used to calculate the ejection fraction. Damage to the muscle of the heart (myocardium), such as that sustained during myocardial infarction or in cardiomyopathy, impairs the heart's ability to eject blood and therefore reduces the ejection fraction.

The term "left ventricular end diastolic diameter (LVEDD)" refers to the cross-sectional diameter of the left ventricle including the septum and posterior wall thicknesses in diastole.

The New York Heart Association (NYHA) Functional Classification provides a simple way of classifying the extent of heart failure. It places patients in one of four categories (classes I-IV) based on how much they are limited during physical activity; the limitations/symptoms are in regards to normal breathing and varying degrees in shortness of breath and or angina pain (class I: no symptoms and no limitation in ordinary physical activity, e.g. shortness of breath when walking, climbing stairs etc./class IV: severe limitations; symptoms even while at rest; mostly bedbound patients).

Brain natriuretic peptide (BNP) is a 32 amino acid polypeptide secreted by the ventricles of the heart in response to excessive stretching of heart muscle cells (cardiomyocytes). BNP is co-secreted along with a 76 amino acid N-terminal fragment (NT proBNP), which is biologically inactive. Both BNP and NT proBNP are used for the diagnosis of heart failure. Their plasma concentrations are typically increased in patients with left ventricular dysfunction.

Reference is made to the figures, wherein

Figure 4:
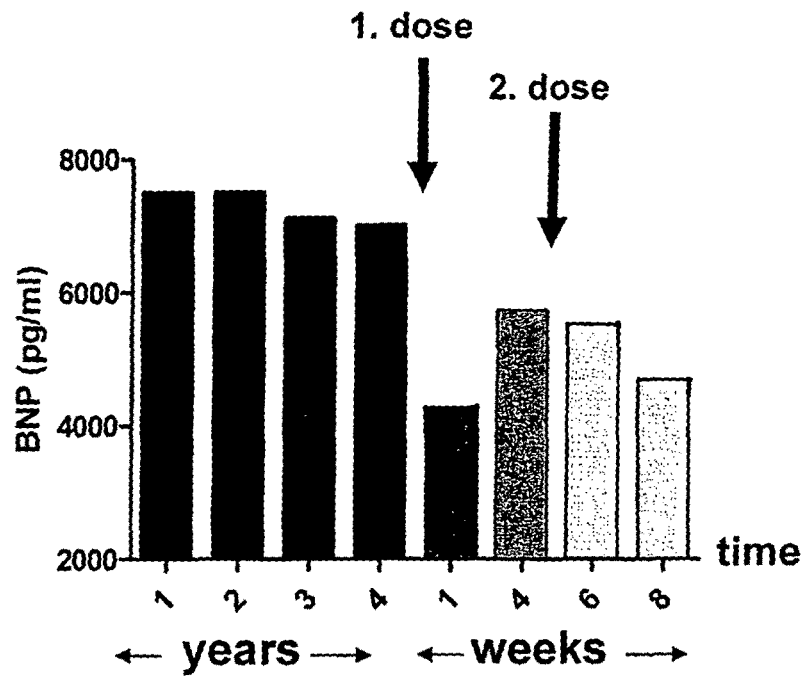
Figure 4:
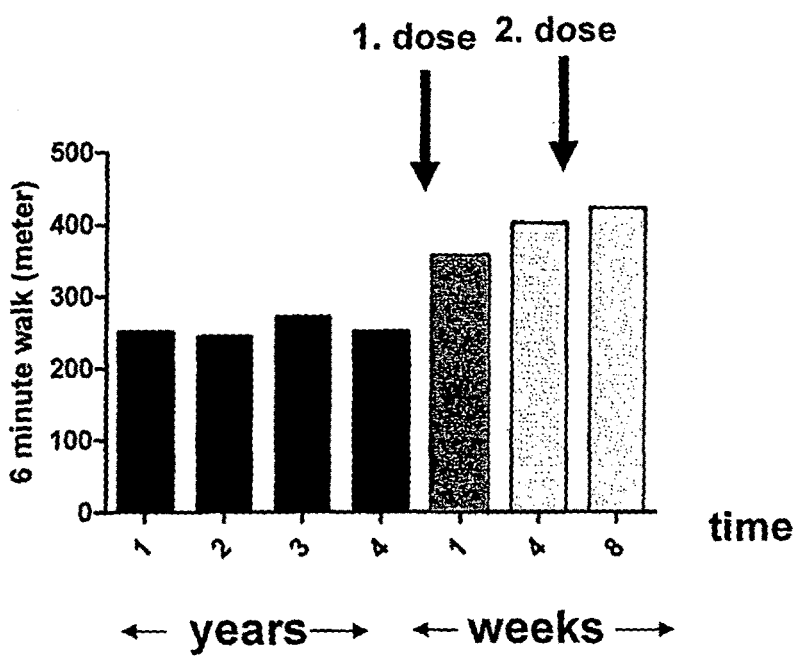
Figure 5:
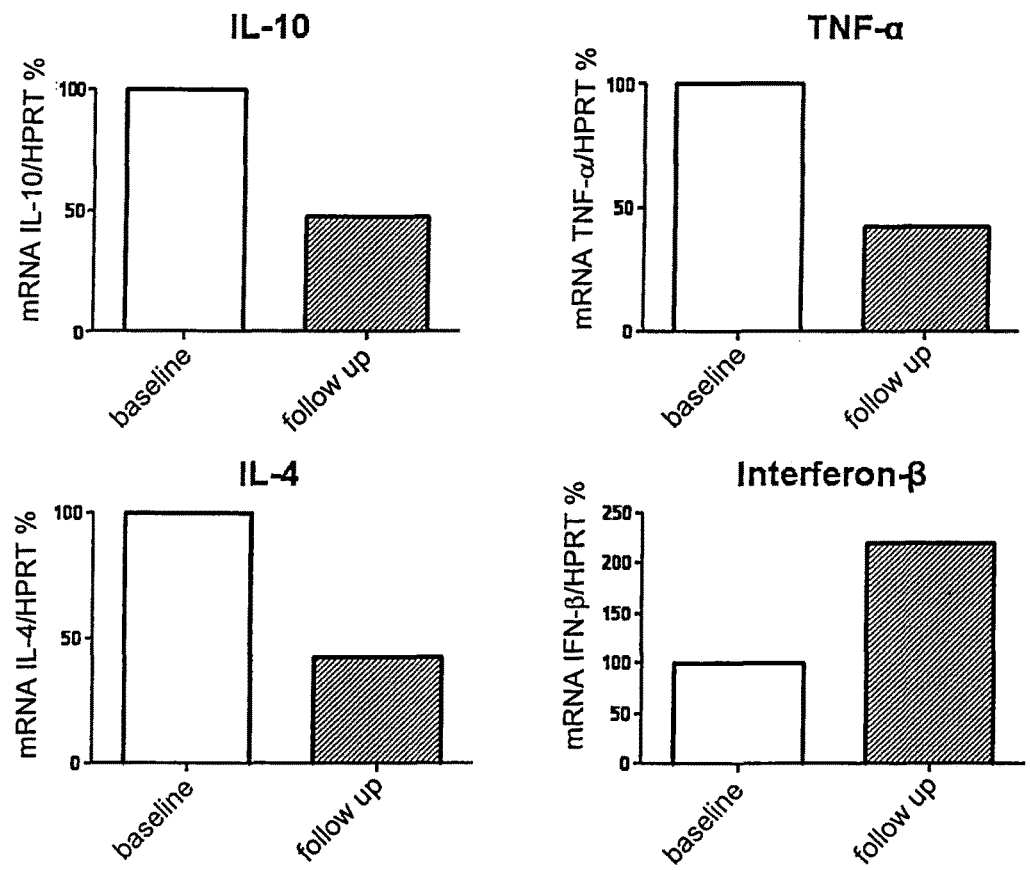

FIG. 4 shows the changes of NT proBNP levels (panel A) and of the performance in the 6-minute walk test (panel B) of a 73-year old female patient with DCMi in response to the treatment with two doses of RITUXAN (rituximab); and FIG. 5 shows the mRNA expression profile of the cytokines TNF-α, IL-4, IL-10 and interferon-β in endomyocardial biopsy at baseline and after treatment with RITUXAN ("follow up"), as shown by quantitative RT-PCR using phosphoribosyl transferase (HPRT) as a standard/control.

The present invention will now be further illustrated by the following three examples from which further features, embodiments and advantages of the present invention may be taken.

EXAMPLE 1

Detection of B-Lymphocyte in Patients Suffering from Cardiac Insufficiency

Endomyocardial biopsies were obtained from the RV septum, frozen in liquid nitrogen, and stored at −80° C. Specimens were embedded in Tissue Tec® (SLEE, Mainz, Germany), and immediately snap-frozen in methylbutane cooled in liquid nitrogen. Embedded specimens were cut serially into cryosections of 5 µm thickness and placed on 10% poly-L-lysine precoated slides. Following 10 minutes of fixation in cold acetone and subsequent air drying, endogenous peroxidase activity was quenched by incubating cryosections with 0.3% $H_2O_2$ in phosphate-buffered saline for 20 minutes.

For immunohistological staining the CD20 monoclonal mouse antibody clone 8J662 (Fa. Biomol, Hamburg, Germany) was used for 45 minutes in a humidified chamber. The EnVision™ peroxidase-conjugated rabbit-anti-mouse antibody (DakoCytomation, Hamburg, Germany) was used as the secondary antibody for 30 min in a humidified chamber. Immunohistological staining was visualized using 3-amino-9-ethylcarbazole (Merck, Darmstadt, Germany). The slides were mounted with Kaiser's gelatine (Merck, Darmstadt, Germany).

Figure 1:
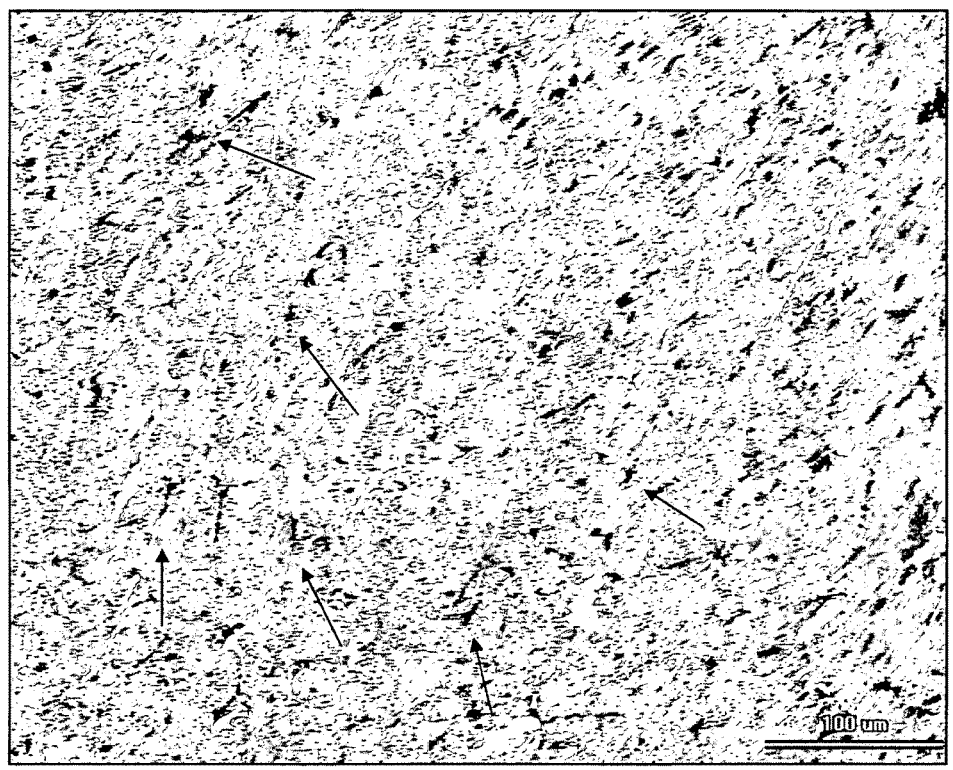
FIG. 1 shows a endomyocardial biopsy specimen from a patient with DCMi, which has been stained with a CD20-antibody (200× magnification)

Upon visual analysis of the treated sections, infiltrations of CD20-positive cells could be observed (see FIG. 1, CD20-positive cells are indicated by black arrows). Such cellular infiltrations were forming cell nests which were located in the intercellular space between the heart muscle cells and the cells of the heart vasculature.

Figure 2:
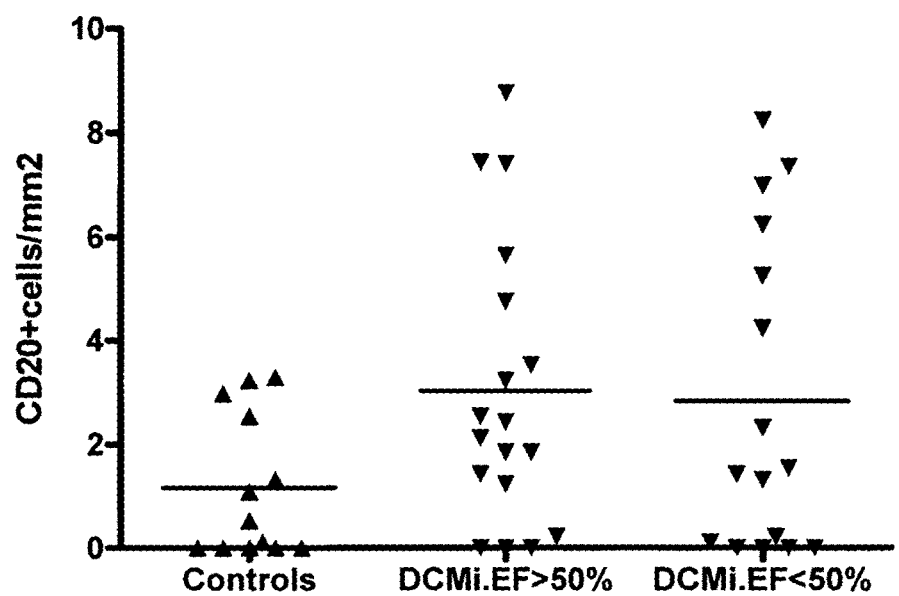
FIG. 2 shows the number of CD20-positive cells per $mm^2$ in endomyocardial biopsies of patients suffering from DCMi with an ejection fraction (EF) >50% or <50%, as compared to patients without DCMi (controls)

As shown in FIG. 2, the number of CD20-positive cells was significantly increased in patients suffering from inflammatory dilated cardiomyopathy (DCMi) with an ejection fraction above or below 50%, as compared to the control specimens.

EXAMPLE 2

Treatment of a Male Patient Suffering from Inflammatory Dilated Cardiomyopathy (DCMi)

A 76-year old male with a 3-year history of cardiac insufficiency due to DCMi (end stage DCM, severe DCMi; mild cardiac inflammation, no cardiac viral persistence, CD20-positive in cardiac biopsy species, NYHA III, EF 20%; LVEDD 71 mm) was treated with RITUXAN using the dosage regimen recommended by the manufacturer. After administration of the first single dose of RITUXAN, the symptoms and LV function (EF 29%) improved already after 24h and stayed stable after the second administration of RITUXAN following the protocol. Stress echocardiographic examinations revealed an additional increase of LV function reserve as compared to examinations performed before RITUXAN had been applied.

EXAMPLE 3

Treatment of a Female Patient Suffering from Inflammatory Dilated Cardiomyopathy (DCMi)

The patient is a 73-year old female with a 5-year history of heart failure symptoms because of severe dilated cardiomyopathy (EF 24%), which continued to persist despite heart failure medication and biventricular ICD-stimulation (NYHA class III).

The female patient was treated with heart failure medication and 375 mg/m² body surface area RITUXAN (rituximab) in two sessions.

Figure 3:
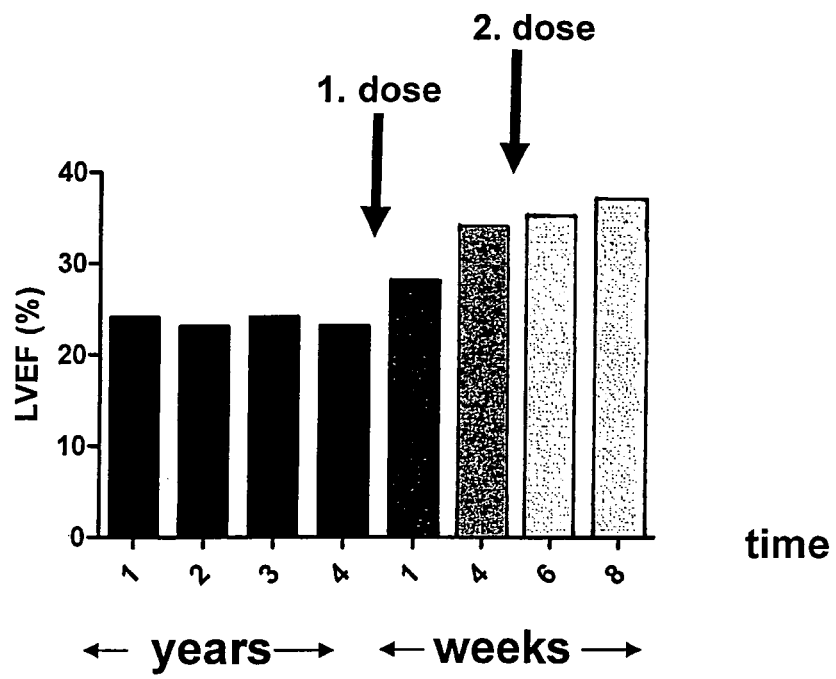
FIG. 3 shows the changes of the left ventricular ejection fraction (LVEF, panel A) and of the left ventricular end diastolic diameter (LVEDD, panel B) of a 73-year old female patient with DCMi in response to the treatment with two doses of RITUXAN (rituximab), as measured by echocardiography.
Figure 3:
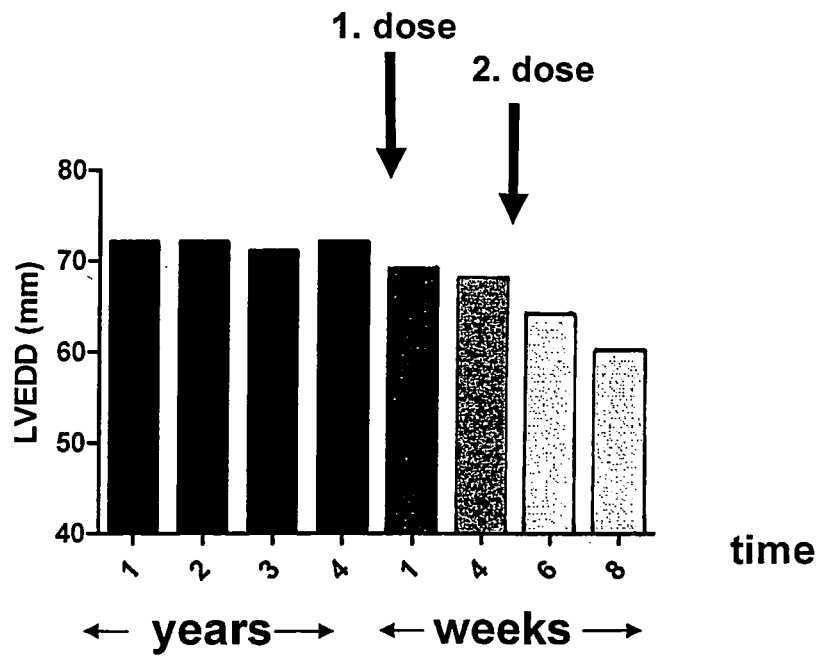

Echocardiography revealed that the left ventricular ejection fraction (LVEF) was significantly increased after the first dose of RITUXAN and further increased after the second dose of RITUXAN (FIG. 3 A). Concomitantly, the left ventricular end diastolic diameter (LVEDD) was decreased (FIG. 3 B). Individual measurements are given in Table 1.

BNP levels were considerably reduced after treatment with RITUXAN (FIG. 4 A). RITUXAN treatment also improved the patient's performance in the 6-minutes walk test, which evaluates the distance walked within 6 minutes (FIG. 4 B).

Subsequent endomyocardial biopsy revealed a partial depletion of B-lymphocytes due to the treatment with RITUXAN (data not shown) and a decrease in the mRNA expression of proinflammatory cytokines, such as TNF-α, IL-4 and IL-10, associated with an increase in the mRNA expression of cytokines with anti-viral potencies, such as interferon-β (see FIG. 5).

TABLE 1

Individual measurements of LVEF/EF and LVEDD (and the resulting NYHA class) of a 73-year old female suffering from DCMi after treatment with Rituxan.

|  | day 0 | day 5 | day 7 | day 12 | day 65 |
| --- | --- | --- | --- | --- | --- |
| EF | 24 | 28 | 28 | 34 | 37 |
| LVEDD | 72 | 71 | 64 | 62 | 60 |
| NYHA class | III | II | II | II | I(-II) |

The features of the present invention disclosed in the specification, the claims and/or the drawings may both separately and in any combination thereof be material for realizing the invention in various forms thereof.

The invention claimed is:

1. A method for treating cardiac insufficiency in a patient, wherein the cardiac insufficiency is caused by dilated inflammatory cardiomyopathy (DCMi), and wherein said method comprises the steps of:
    obtaining heart tissue from a patient via an endomyocardial biopsy;
    determining the presence of B-lymphocytes in the heart tissue obtained via the endomyocardial biopsy using a B-lymphocyte targeting agent; and
    diagnosing the patient with cardiac insufficiency caused by DCMi based on the presence of B-lymphocytes in the heart tissue;
    and wherein said method further comprises administering a B-lymphocyte targeting agent to the patient having been diagnosed with cardiac insufficiency caused by DCMi, wherein the B-lymphocyte targeting agent binds to, or targets, human CD20, and wherein the B-lymphocyte targeting agent is selected from antibodies, aptamers, spiegelmers, antigen binding polypeptides and anticalines.

2. The method according to claim 1, wherein the B-lymphocytes are present in intercellular space between heart muscle cells and cells of heart vasculature.

3. The method according to claim 1, wherein the B-lymphocyte targeting agent is capable of killing B-lymphocytes.

4. The method according to claim 3, wherein the B-lymphocytes bear at least one antigen selected from the group consisting of CD19, CD20 and CD21.

5. The method according to claim 1, wherein the B-lymphocyte targeting agent is a naked B-lymphocyte targeting agent.

6. The method according to claim 3, wherein the B-lymphocyte targeting agent comprises a further moiety that is useful in the killing of the B-lymphocyte.

7. The method according to claim 6, wherein the further moiety is selected from the group consisting of radioisotopes, cytotoxic agents and immunomodulators.

8. The method according to claim 1, wherein the B-lymphocyte targeting agent is administered in an amount such as to provide a therapeutic effect.

9. The method according to claim 1, wherein the B-lymphocyte targeting agent is an antibody.

10. The method according to claim 9, wherein the antibody is a polyclonal antibody.

11. The method according to claim 9, wherein the antibody is a monoclonal antibody.

12. The method according to claim 9, wherein the antibody is an antibody fragment that binds to the same antigen and/or epitope as the respective antibody.

13. The method according to claim 12, wherein the antibody fragment is selected from the group consisting of F(ab')2, F(ab)2, Fab', Fab, Fv, scFv and sFv.

14. The method according to claim 9, wherein the antibody is a subhuman primate antibody, a murine monoclonal antibody, a chimeric antibody, a humanized antibody or a human antibody.

15. The method according to claim 9, wherein the antibody mediates complement-mediated cytotoxicity and/or antibody-dependent cell-mediated cytotoxicity.

16. The method according to claim 9, wherein the antibody is an anti-CD20 antibody.

17. The method according to claim 16, wherein the antibody is rituximab.

18. The method according to claim 1, wherein the B-lymphocyte targeting agent comprises a further moiety which is useful in the killing of the B-lymphocyte.

19. The method according to claim 18, wherein the further moiety is selected from the group consisting of radioisotopes, cytotoxic agents and immunomodulators.

20. The method according to claim 19, wherein the further moiety is a radioisotope.

21. The method according to claim 20, wherein the radioisotope is selected from the group consisting of $^{198}$Au, $^{32}$P, $^{125}$I, $^{131}$I, $^{90}$Y, $^{186}$Re, $^{188}$Re, $^{67}$Cu, $^{211}$At, $^{213}$Bi and $^{225}$Ac.

* * * * *